(12) United States Patent
Hagen et al.

(10) Patent No.: US 11,026,797 B2
(45) Date of Patent: Jun. 8, 2021

(54) JOINT IMPLANT PART, JOINT ENDOPROSTHESIS AND METHOD FOR PRODUCING A JOINT IMPLANT PART AND A JOINT ENDOPROSTHESIS

(71) Applicant: Aesculap AG, Tuttlingen (DE)

(72) Inventors: Thomas Hagen, Tuttlingen (DE); Thomas Grupp, Denkingen (DE)

(73) Assignee: Aesculap AG, Tuttlingen (DE)

( * ) Notice: Subject to any disclaimer, the term of this patent is extended or adjusted under 35 U.S.C. 154(b) by 260 days.

(21) Appl. No.: 15/716,835

(22) Filed: Sep. 27, 2017

(65) Prior Publication Data

US 2018/0014938 A1 Jan. 18, 2018

Related U.S. Application Data

(63) Continuation of application No. PCT/EP2016/057193, filed on Apr. 1, 2016.

(30) Foreign Application Priority Data

Apr. 1, 2015 (DE) .......................... 102015105100

(51) Int. Cl.
*A61F 2/38* (2006.01)
*A61F 2/30* (2006.01)
*A61F 2/32* (2006.01)

(52) U.S. Cl.
CPC .............. *A61F 2/3094* (2013.01); *A61F 2/32* (2013.01); *A61F 2/38* (2013.01); *A61F 2/3859* (2013.01); *A61F 2002/30011* (2013.01); *A61F 2002/30014* (2013.01); *A61F 2002/3092* (2013.01); *A61F 2002/30955* (2013.01); *A61F 2002/30962* (2013.01)

(58) Field of Classification Search
CPC .......... A61F 2/3094; A61F 2002/30011; A61F 2002/30014; A61F 2/32; A61F 2/38
See application file for complete search history.

(56) References Cited

U.S. PATENT DOCUMENTS

| 4,280,233 A | 7/1981 | Raab |
|---|---|---|
| 10,226,347 B2 | 3/2019 | Landon |

(Continued)

FOREIGN PATENT DOCUMENTS

| CN | 1438859 | 8/2003 |
|---|---|---|
| CN | 104203161 | 12/2014 |

(Continued)

*Primary Examiner* — Christopher D. Prone
(74) *Attorney, Agent, or Firm* — Lipsitz & McAllister, LLC

(57) ABSTRACT

The invention relates to a joint implant part of a joint endoprosthesis. The joint implant part comprises at least one first volume region, at least one second volume region and at least one third volume region. The at least one first volume region defines a bone contact surface region with at least one bone contact surface. The at least one second volume region defines a joint surface region with at least one joint surface. The at least one third volume region comprises neither a bone contact surface nor a joint surface. A modulus of elasticity in the at least one first and/or in the at least one second and/or in the at least one third volume region changes continuously or substantially continuously or discontinuously in at least one spatial direction.

19 Claims, 5 Drawing Sheets

(56) References Cited

U.S. PATENT DOCUMENTS

Figure 1:
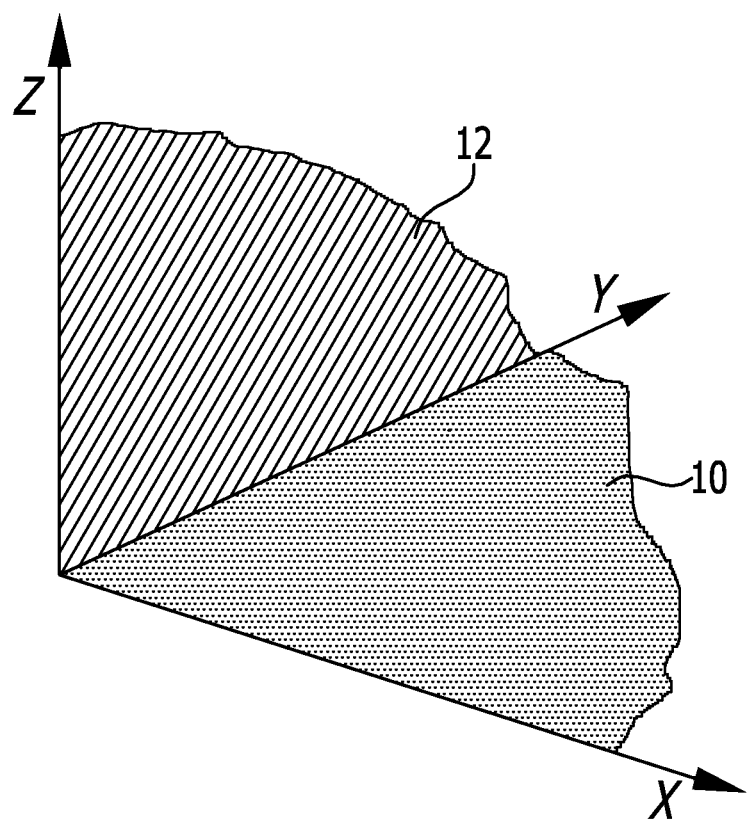

| | | |
|---|---|---|
| 2007/0116734 A1 | 5/2007 | Akash |
| 2010/0268337 A1* | 10/2010 | Gordon .................... A61F 2/28 |
| | | 623/16.11 |
| 2011/0202140 A1 | 8/2011 | Turner et al. |
| 2015/0032218 A1 | 1/2015 | Landon |

FOREIGN PATENT DOCUMENTS

| | | |
|---|---|---|
| CN | 105105875 | 12/2015 |
| DE | 3005265 | 8/1980 |
| DE | 4137383 | 1/1994 |
| DE | 19904436 | 8/2000 |
| DE | 10051438 | 11/2006 |
| EP | 2676636 | 12/2013 |
| EP | 1919402 | 7/2015 |
| GB | 2045082 | 10/1980 |
| WO | 2007053022 | 5/2007 |
| WO | 2013109422 | 7/2013 |

* cited by examiner

JOINT IMPLANT PART, JOINT ENDOPROSTHESIS AND METHOD FOR PRODUCING A JOINT IMPLANT PART AND A JOINT ENDOPROSTHESIS

CROSS-REFERENCE TO RELATED APPLICATIONS

This application is a continuation of international application number PCT/EP2016/057193 filed on Apr. 1, 2016 and claims the benefit of German application number 10 2015 105 100.1 filed on Apr. 1, 2015, which are incorporated herein by reference in their entirety and for all purposes.

FIELD OF THE INVENTION

The present invention relates to a joint implant part of a joint endoprosthesis, which joint implant part comprises at least one first volume region, at least one second volume region and at least one third volume region, which at least one first volume region defines a bone contact surface region with at least one bone contact surface, which at least one second volume region defines a joint surface region with at least one joint surface and which at least one third volume region comprises neither a bone contact surface nor a joint surface.

The present invention further relates to a joint endoprosthesis comprising at least one joint implant part.

Furthermore, the present invention relates to a method for producing a joint implant part of a joint endoprosthesis, which joint implant part is formed with at least one first volume region, at least one second volume region and at least one third volume region, which at least one first volume region is made in the form of a bone contact surface region with at least one bone contact surface, which at least one second volume region is made in the form of a joint surface region with at least one joint surface, and which at least one third volume region is formed neither with a bone contact surface nor with a joint surface.

The present invention also relates to a method for producing a joint endoprosthesis comprising at least one joint implant part.

BACKGROUND OF THE INVENTION

Joint implant parts and joint endoprostheses of the kind described at the outset are known in various configurations. They are produced from approved implant materials.

A problem in known joint endoprostheses is that micromovements may occur between bone contact surfaces of the joint implant parts and the bone prepared for contact with a joint implant part. In particular, characteristics of the material from which the joint implant part is made are the reason for this. These differ, as a rule, significantly from characteristics of the prepared bone. Micromovements do, however, negatively affect the durability of the connection between the joint implant part and the prepared bone.

SUMMARY OF THE INVENTION

In a first aspect of the invention, a joint implant part of a joint endoprosthesis is provided. The joint implant part comprises at least one first volume region, at least one second volume region and at least one third volume region. The at least one first volume region defines a bone contact surface region with at least one bone contact surface. The at least one second volume region defines a joint surface region with at least one joint surface. The at least one third volume region comprises neither a bone contact surface nor a joint surface. A modulus of elasticity in the at least one first and/or in the at least one second and/or in the at least one third volume region changes continuously or substantially continuously or discontinuously in at least one spatial direction.

In a second aspect of the invention, a joint endoprosthesis comprises at least one joint implant part, wherein the at least one joint implant part comprises at least one first volume region, at least one second volume region and at least one third volume region. The at least one first volume region defines a bone contact surface region with at least one bone contact surface. The at least one second volume region defines a joint surface region with at least one joint surface. The at least one third volume region comprises neither a bone contact surface nor a joint surface. A modulus of elasticity in the at least one first and/or in the at least one second and/or in the at least one third volume region changes continuously or substantially continuously or discontinuously in at least one spatial direction.

In a third aspect of the invention, a method for producing a joint implant part of a joint endoprosthesis is provided. The joint implant part is formed with at least one first volume region, at least one second volume region and at least one third volume region. The at least one first volume region is made in the form of a bone contact surface region with at least one bone contact surface. The at least one second volume region is made in the form of a joint surface region with at least one joint surface. The at least one third volume region is formed neither with a bone contact surface nor with a joint surface. The at least one first and/or the at least one second and/or the at least one third volume region is/are formed with a modulus of elasticity which changes continuously or substantially continuously or discontinuously in at least one spatial direction.

In a forth aspect of the invention, a method for producing a joint endoprosthesis comprising at least one joint implant part is provided. The joint implant part is formed with at least one first volume region, at least one second volume region and at least one third volume region. The at least one first volume region is made in the form of a bone contact surface region with at least one bone contact surface. The at least one second volume region is made in the form of a joint surface region with at least one joint surface. The at least one third volume region is formed neither with a bone contact surface nor with a joint surface. The at least one first and/or the at least one second and/or the at least one third volume region is/are formed with a modulus of elasticity which changes continuously or substantially continuously or discontinuously in at least one spatial direction.

BRIEF DESCRIPTION OF THE DRAWING FIGURES

Figure 2:
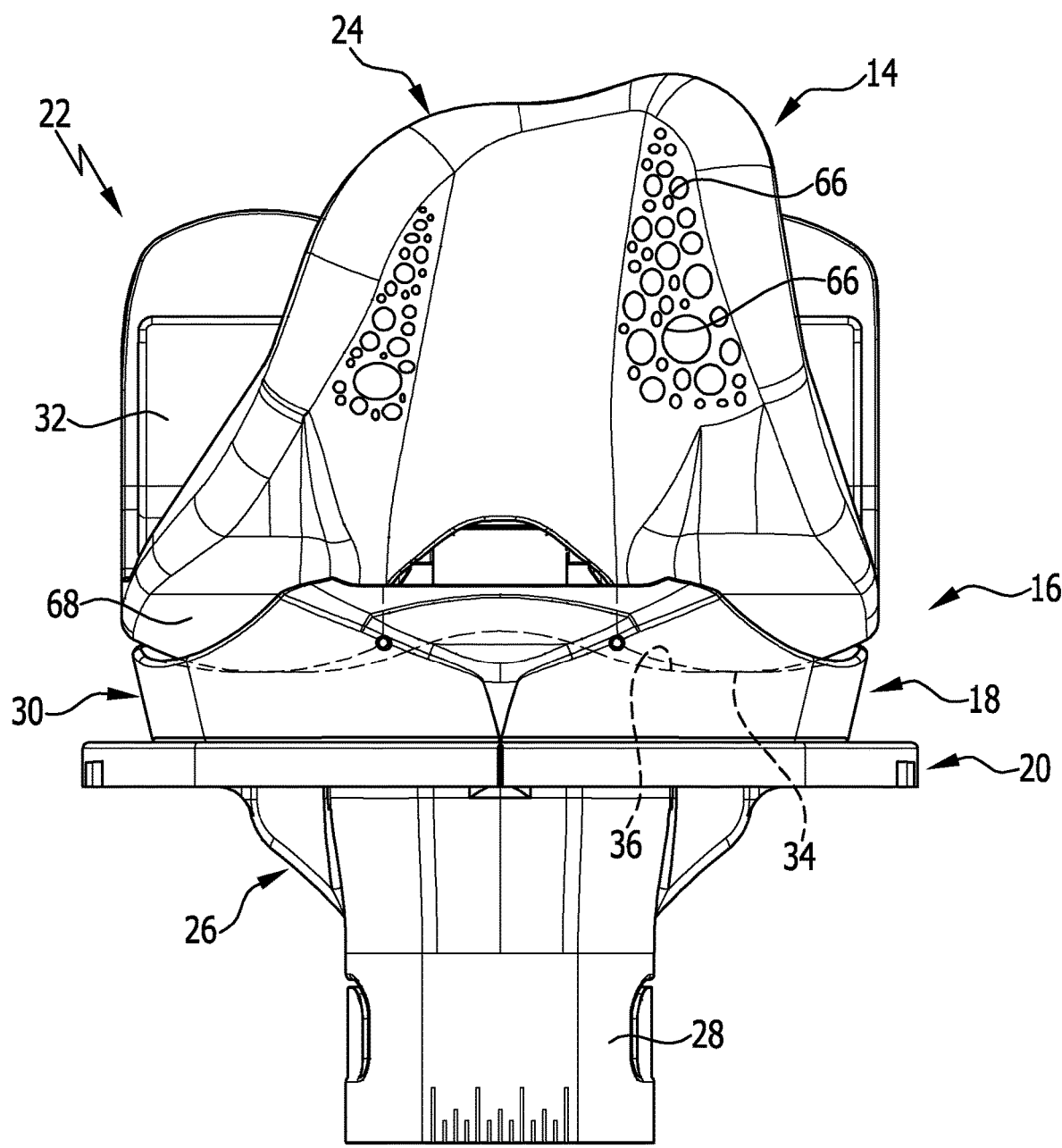
Figure 3:
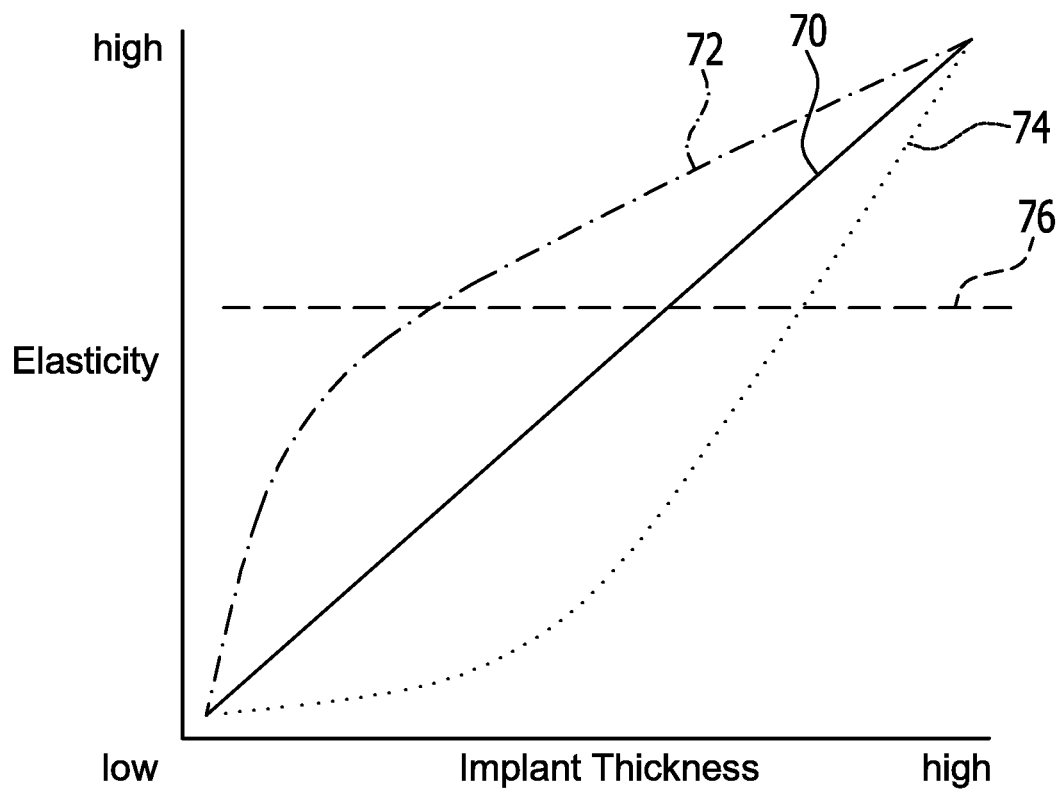
Figure 4:
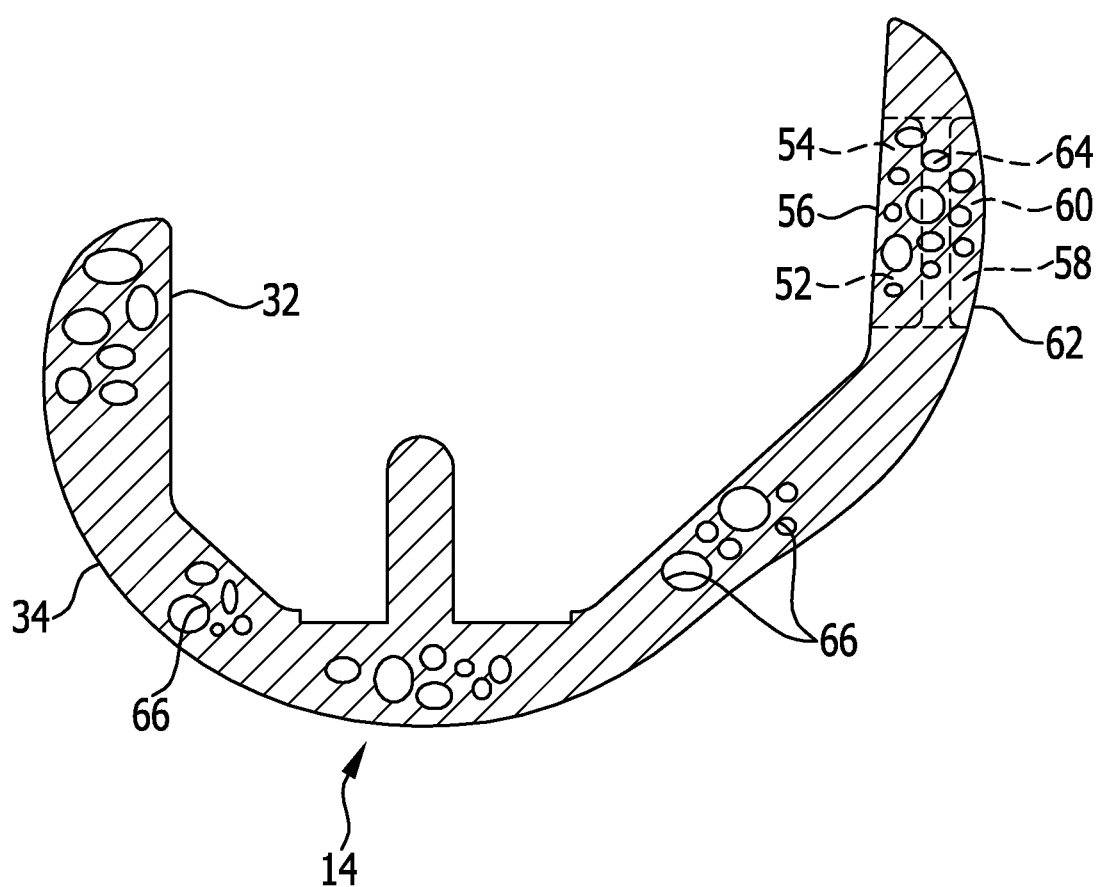

The foregoing summary and the following description may be better understood in conjunction with the drawing figures, of which:

FIG. 1: a schematic representation of two possible sections through a three-dimensional joint implant part;

FIG. 2: a schematic perspective view of a joint implant part;

FIG. 3: a schematic representation of different extents of elasticity of a joint implant part in dependence upon an implant thickness;

FIG. 4: a schematic sectional view through a joint implant part; and

Figure 5:
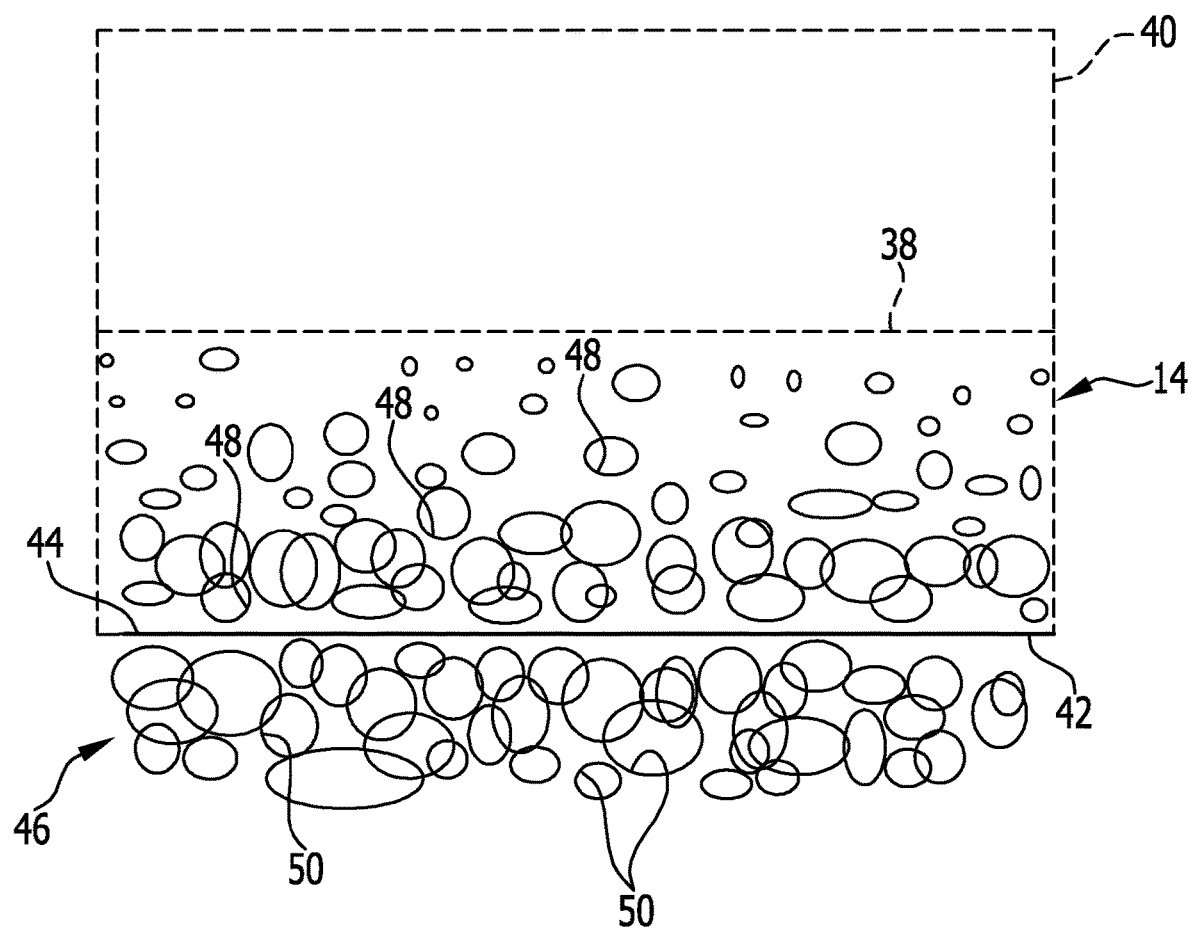

FIG. 5: a detail view in the area of transition between a joint implant and a bone.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a joint implant part of a joint endoprosthesis, which joint implant part comprises at least one first volume region, at least one second volume region and at least one third volume region, which at least one first volume region defines a bone contact surface region with at least one bone contact surface, which at least one second volume region defines a joint surface region with at least one joint surface and which at least one third volume region comprises neither a bone contact surface nor a joint surface, wherein a modulus of elasticity in the at least one first and/or in the at least one second and/or in the at least one third volume region changes continuously or substantially continuously or discontinuously in at least one spatial direction.

The solution proposed in accordance with the invention enables, in particular, joint implant parts to be formed in such an optimized way that in the transition from the implant part to the bone, i.e., in the bone contact surface region and, in particular, at the bone contact surface, an elasticity of the joint implant part is adapted to an elasticity of the prepared bone. In this way, it is possible to prevent micromovements which may occur in conventional joint implant parts produced from a material having a uniformly distributed structure with a corresponding elasticity. In particular, the proposed development makes it possible to adjust elasticities of the different volume regions of the joint implant part differently and, in addition, to also change these in the respective volume regions in the stated way in order to predefine, for example, continuous changes in the modulus of elasticity both within the joint implant part and in the transition to a bone or another joint implant part. In this way, the joint implant part can be optimally adapted to the bone and to a further joint implant part for formation of the joint endoprosthesis, in order to adapt, as a whole, in particular, a structure and/or a function of the joint implant to the original joint. A long-lasting stability of the joint endoprosthesis can thereby be improved in comparison with conventional known endoprostheses.

Furthermore, it is expedient, in particular, also in a joint implant part of the kind described at the outset, for a firmness in the at least one first and/or in the at least one second and/or in the at least one third volume region to change continuously or substantially continuously or discontinuously in at least one spatial direction. The changing of the firmness in the stated way in at least one of the three different volume regions allows, in particular, regions of the joint implant part to be formed with a higher or lower degree of firmness in accordance with the firmness requirements. In doing so, changes in firmness can be effected continuously or discontinuously. In particular, regions with less firmness can, for example, be made less solid than is the case in conventional joint implant parts which, as a rule, are made from a material with an evenly distributed structure. In this way, joint implant parts can be formed, which are as close as possible in their structure to a natural joint part which they are to replace.

The at least one first volume region preferably has an elasticity with a modulus of elasticity, in particular, in the region of the at least one bone contact surface, which corresponds or corresponds substantially to a modulus of elasticity of a bone of a human being or an animal. If, in particular, the modulus of elasticity in the bone contact surface region and in the region of the bone contact surface corresponds or corresponds substantially or comes close to a modulus of elasticity of a bone of a human being or an animal, to which the joint implant part is to be fixed with the bone contact surface, there is then a continuous or substantially continuous transition of the modulus of elasticity of the joint implant part, on the one hand, and of the bone, on the other hand. In particular, micromovements between the joint implant part and the bone can thereby be minimized or even eliminated completely.

A modulus of elasticity of the at least one first and/or of the at least one second and/or of the at least one third volume region preferably lies in a range of from approximately 0.2 $kN/mm^2$ to approximately 100 $kN/mm^2$. The modulus of elasticity preferably lies in a range of from approximately 0.2 $kN/mm^2$ to approximately 20 $kN/mm^2$. The providing of a modulus of elasticity in the stated ranges for at least one of the at least three volume regions makes it possible, in particular, to adapt the elasticity of the joint implant part to a natural bone in a simple way.

It is advantageous for the firmness of the at least one first and/or of the at least one second and/or of the at least one third volume region to lie in a range of from approximately 0.2 $kN/mm^2$ to approximately 100 $kN/mm^2$. The firmness preferably lies in a range of from approximately 0.2 $kN/mm^2$ to approximately 20 $kN/mm^2$. The providing of firmnesses in the stated ranges makes it possible, in particular, to make implant parts sufficiently stable in the regions in which a higher degree of firmness is required, but to minimize a firmness in regions which require only a low degree of firmness, for example, in order to save material and, consequently, weight. In particular, in the case of revision implants, for example, in the knee area, a conventional joint implant part can weigh several kilograms, which is experienced as unpleasant by patients. Joint implant parts can be made significantly lighter by the proposed development, as firmnesses can be predefined and optimized in dependence upon the implant shape, for example, by FEM calculations.

An adaptation of the joint implant part to the requirements of a patient can be further improved if the at least one first volume region has an inner structure which corresponds substantially to an inner construction of a bone of a human being or an animal. For example, bone trabeculae can be replicated in artificial joint implant parts. This is, in particular, one possibility of adapting an elasticity and/or a firmness of the bone contact surface region and the bone contact surface to characteristics of a natural bone. Micromovements are thus minimized, and so loosenings of the implanted joint implant part are substantially eliminated.

In order to simplify the implantation and also improve stability of the joint implant part, it is advantageous for the joint implant part to be of one-piece formation. Since no further connections are required, a weight of the joint implant part can thus also be minimized.

The joint implant part can be produced in a particularly simple way if it is produced by sintering from at least one sinterable material. In particular, it can be produced by laser sintering. The joint implant part may, however, also be sintered from several materials which, for example, are used to form different volume regions.

It is expedient for the joint implant part to be produced from at least two materials. In particular, these can be mixed before the sintering, for example, the laser sintering. In this way, characteristics of a natural bone can be replicated even better.

The at least one sinterable material is preferably a metal and/or a plastic material. It is, for example, thus possible for metals and plastic materials to be mixed and formed into a joint implant in a single method step, for example, by sintering.

The metal is preferably cobalt, chromium and/or molybdenum or contains one or more of the aforementioned metals. It is, for example, thus possible for joint implants to be formed from metals which are already approved as implant materials.

It is expedient for the plastic material to be or contain polyetheretherketone. Polyetheretherketone (PEEK) is particularly well suited as implant material and, in particular, makes it possible to adjust elasticities and firmnesses in a joint implant part, which correspond to those of a natural bone.

In order to be able to adjust, in particular, elasticities and/or firmnesses of different volume regions of the joint implant part as individually as possible, it is expedient for the at least one first and/or the at least one second and/or the at least one third volume region to be formed from different materials. For example, the first volume region can be formed from a metal, the second from a ceramic material and the third from a mixture of a metal and a plastic material.

In accordance with a further preferred embodiment of the invention, it may be provided that a proportion of different materials in the transition between two of the three different volume regions changes continuously or substantially continuously or changes discontinuously in at least one spatial direction. In particular, with a continuous or substantially continuous change in a proportion of the different materials in the transition between two of the three volume regions, a homogeneous joint implant part can, as a whole, be formed. Here homogeneous is, in particular, not to be understood as meaning that the total volume defined by the joint implant part has a uniform structure.

In order to make the joint implant part as light as possible, it is advantageous for the at least one first volume region and/or the at least one second volume region and/or the at least one third volume region to comprise at least one cavity. In particular, several cavities may be provided or also a plurality of cavities which are connected to one another or separated from one another. If several cavities are provided, these may be of substantially the same size or also have significantly different sizes and shapes.

In particular, it is expedient for the at least one cavity to be in the form of a closed, completely enclosed cavity. In this way, it is possible to prevent bone material from growing into the cavity or materials introduced into the cavity before formation of the joint implant part or during formation thereof from being able to get outside and into the body of a patient.

It is expedient for a plurality of cavities to be formed, and for a total volume defined by the plurality of cavities in the at least one third volume region to be greater than in the at least one first and/or in the at least one second volume region. The at least one third volume region, which defines neither a bone contact surface nor a joint surface, can thus be formed with a cavity volume of maximum size, for example, in order to facilitate the ingrowth of bone, if the plurality of cavities are in fluid communication with one another, or in order to minimize a weight of the joint implant part, in particular, by the number and/or the volume of the cavities being maximized where only low degrees of firmness are required.

In order to improve a connection between the joint implant part and a bone, it is advantageous for a plurality of cavities to be formed, and for at least some of the cavities to be in fluid communication with one another. Furthermore, cavities in fluid communication with one another enable, in particular, also optimized cleaning of the joint implant part after it has been produced. In addition, other materials and possibly also medicines can be introduced directly into cavities of the joint implant part.

In order to improve a connection of the joint implant part in the area of the bone contact surface region with the prepared bone of the patient, it is advantageous for the at least one cavity to be in the form of a depression of the bone contact surface.

The at least one joint surface is preferably in the form of a closed layer of material and/or it is smooth and/or it is polished. This enables, in particular, joint implant parts to be formed with optimized joint surfaces. For example, a volume region of the joint implant part, which does not define a joint surface, may be formed from a different material than a second volume region of the joint implant part. For example, the second volume region may be formed from a ceramic material, the third volume region from a metal. A transition between both volume regions may be continuous, substantially continuous or discontinuous.

In accordance with a further preferred embodiment of the invention, it may be provided that the joint implant part is in the form of a femur part of a knee joint endoprosthesis, which is fixable to a femur, or in the form of a tibia part of a knee joint endoprosthesis, which is fixable to a tibia, or in the form of a part of a hip joint, ankle joint, elbow joint or shoulder joint endoprosthesis. In principle, joint implant parts of any joints of the human body can be formed in the manner proposed in accordance with the invention, also the intervertebral implants not yet mentioned.

The present further invention relates to a joint endoprosthesis comprising at least one joint implant part, wherein the at least one joint implant part comprises at least one first volume region, at least one second volume region and at least one third volume region, which at least one first volume region defines a bone contact surface region with at least one bone contact surface, which at least one second volume region defines a joint surface region with at least one joint surface and which at least one third volume region comprises neither a bone contact surface nor a joint surface, wherein a modulus of elasticity in the at least one first and/or in the at least one second and/or in the at least one third volume region changes continuously or substantially continuously or discontinuously in at least one spatial direction.

It is expedient for the joint endoprosthesis to be in the form of a knee joint, hip joint, ankle joint, elbow joint or shoulder joint endoprosthesis. Practically all joints of the body of a human being or an animal can thus be replaced by joint endoprostheses which are optimally adapted to characteristics of the bone to which they are connected.

The present further invention relates to a method for producing a joint implant part of a joint endoprosthesis, which joint implant part is formed with at least one first volume region, at least one second volume region and at least one third volume region, which at least one first volume region is made in the form of a bone contact surface region with at least one bone contact surface, which at least one second volume region is made in the form of a joint surface region with at least one joint surface, and which at least one third volume region is formed neither with a bone contact surface nor with a joint surface, wherein the at least one first and/or the at least one second and/or the at least one third volume region is/are formed with a modulus of elasticity which changes continuously or substantially continuously or discontinuously in at least one spatial direction.

The method proposed in accordance with the invention makes it possible, in particular, to form a joint implant part such that it has, for example, an elasticity in the region of a bone contact surface, which corresponds to an elasticity of the natural bone. As already explained in detail above, micromovements between the joint implant part and the bone after the implantation can thus be prevented or at least significantly reduced. In comparison with conventional joint implant parts, the risk of loosenings of the joint implant part owing to the micromovements can thus be minimized or even completely eliminated.

Furthermore, it may be advantageous, in particular, also in a method of the kind described at the outset, that the at least one first and/or the at least one second and/or the at least one third volume region is/are formed with a firmness which changes continuously or substantially continuously or discontinuously in at least one spatial direction. The development of the known method in the proposed manner makes it possible, in particular, to form the joint implant part with different firmnesses. In particular, the at least three defined volume regions may have different firmness. Joint implant parts can thus be optimized, in particular, with respect to their weight.

To enable optimum adaptation of the joint implant to a bone, it is advantageous for the at least one first volume region to be formed with an elasticity with a modulus of elasticity, in particular, in the region of the at least one bone contact surface, which corresponds to a modulus of elasticity of a bone of a human being or an animal.

To enable adaptation of the joint implant part to a bone of a human being or an animal, which is as optimal as possible, it is expedient for the at least one first and/or the at least one second and/or the at least one third volume region to be formed with a modulus of elasticity, which lies in a range of from approximately 0.2 kN/mm$^2$ to approximately 100 kN/mm$^2$. The modulus of elasticity preferably lies in a range of from approximately 0.2 kN/mm$^2$ to approximately 20 kN/mm$^2$.

To be able to ensure a sufficient firmness of the joint implant part, it is advantageous for the at least one first and/or the at least one second and/or the at least one third volume region to be formed with a firmness, which lies in a range of from approximately 0.2 N/mm$^2$ to approximately 100 N/mm$^2$. The firmness preferably lies in a range of from approximately 0.2 kN/mm$^2$ to approximately 20 kN/mm$^2$.

Furthermore, it may be expedient for the at least one first volume region to be formed with an inner structure which corresponds substantially to an inner construction of a bone of a human being or an animal. In particular, bone trabeculae of the natural bone can be replicated by suitable materials, for example, metals or plastic materials.

The joint implant part is preferably formed in one piece. It can then be produced in one step, whereby productions costs can be lowered.

The joint implant part is expediently produced by sintering from at least one sinterable material. In particular, the joint implant part can be produced by laser sintering. For example, the sintering can also be carried out in the course of so-called 3D printing in order to produce the joint implant part in the course of an additive manufacturing process. Two or more different sinterable materials may, of course, also be used to form the joint implant part.

It is expedient for the joint implant part to be produced from at least two materials which are mixed before the sintering. The mixture may be homogeneous or inhomogeneous, depending on whether a homogeneous structure of the joint implant part is desired or not.

At least one metal and/or at least one plastic material is/are preferably used as the at least one sinterable material. In particular, these may be biocompatible materials.

The method can be easily performed if titanium, cobalt, chromium and/or molybdenum or a mixture of two or more of these metals or alloys of these metals is/are used as the at least one metal. These metals are particularly well suited as implant materials and have the necessary biocompatibility.

The method can also be easily and cost-effectively performed if polyetheretherketone is used as the at least one plastic material. Polyetheretherketone (PEEK) is particularly well suited as implant material and can be processed very well, in particular, also in a mixture with a metal powder.

It is advantageous for the at least one first and/or the at least one second and/or the at least one third volume region to be formed from different materials. In this way, joint implant parts can be optimally designed, in particular, in the area of a joint surface and also in the area of a bone contact surface. In addition, a weight of the joint implant part can be minimized if very light materials are used, in particular, in the at least one third volume region.

In accordance with a further preferred variant of the method, it may be provided that the joint implant part is formed such that a proportion of different materials in the transition between two of the three different volume regions changes continuously or substantially continuously or changes discontinuously in at least one spatial direction. This method variant enables, in particular, particularly stable joint implant parts to be formed as discontinuous changes in the materials are not absolutely necessary. Rather, different materials, similarly to tissue that has grown together, can penetrate one another and thus optimize a stability of the joint implant part.

Furthermore, it is advantageous for the at least one first volume region and/or the at least one second volume region and/or the at least one third volume region to be formed with at least one cavity. On the one hand, material can thereby be saved, which helps to reduce the weight of the joint implant part, and, on the other hand, cavities can thereby also be used, into which bone or body tissue can grow, in order to improve a connection of the joint implant part to a bone.

It is expedient for the at least one cavity to be made in the form of a closed, completely enclosed cavity. In this way, for example, fillers introduced into the cavity can, in particular, be prevented from being able to come out. This is of importance, in particular, if the fillers are not biocompatible fillers.

It is advantageous for a plurality of cavities to be formed such that a total volume defined by the plurality of cavities in the at least one third volume region is greater than in the at least one first and/or in the at least one second volume region. In particular, the at least one third volume region can be formed at maximum hollow. This helps to reduce a weight of the joint implant part. Preferably, those regions of the joint implant part for which only low firmness requirements have to be met are provided with a large number of cavities with a large total volume.

It is expedient for a plurality of cavities to be formed such that at least some of the cavities are in fluid communication with one another. The performing of the method in this way enables, in particular, bone or tissue to grow into the cavities in fluid communication with one another.

The method can be performed particularly easily if the at least one cavity is made in the form of a depression of the bone contact surface. For example, this can be formed in the course of the sintering or subsequently by drilling, milling or any other machining with material removal.

A joint endoprosthesis with particularly long-lasting stability can be achieved if the at least one joint surface is made in the form of a closed layer of material and/or is formed so as to be smooth and/or is formed so as to be polished. In this way, friction between the joint implant part and a further joint implant part interacting with it to form the joint endoprosthesis can be minimized.

In order to be able to replace any damaged natural joints of human beings or animals, it is advantageous for the joint implant part to be made in the form of a femur part of a knee joint endoprosthesis, which is fixable to a femur, or in the form of a tibia part of a knee joint endoprosthesis, which is fixable to a tibia, or in the form of a part of a hip joint, ankle joint, elbow joint or shoulder joint endoprosthesis.

The present further invention relates to a method for producing a joint endoprosthesis comprising at least one joint implant part, wherein the at least one joint implant part is produced by a method according to which the joint implant part is formed with at least one first volume region, at least one second volume region and at least one third volume region, which at least one first volume region is made in the form of a bone contact surface region with at least one bone contact surface, which at least one second volume region is made in the form of a joint surface region with at least one joint surface, and which at least one third volume region is formed neither with a bone contact surface nor with a joint surface, wherein the at least one first and/or the at least one second and/or the at least one third volume region is/are formed with a modulus of elasticity which changes continuously or substantially continuously or discontinuously in at least one spatial direction.

The joint endoprosthesis is preferably made in the form of a knee joint, hip joint, ankle joint, elbow joint or shoulder joint endoprosthesis. Essentially all relevant larger joints that are damaged as a result of trauma or wear can thus be replaced by an artificial joint endoprosthesis.

In order to simplify the representability of a new three-dimensional component geometry, the spatial relationships are represented in two surface geometries respectively in FIG. 1. These are, on the one hand, the xy-plane 10 and, on the other hand, the yz-plane 12. The xy-plane 10 symbolizes, for example, the view of an implant surface, the yz-plane 12 a cross section through an implant thickness.

A joint implant part 14 of a joint endoprosthesis, designated in its entirety by reference numeral 16, is represented schematically in FIG. 2. The joint endoprosthesis 16 further comprises two further joint implant parts 18 and 20. The joint endoprosthesis 16 is represented schematically in FIG. 2 as a knee joint endoprosthesis 22 with a femur part 24 for anchoring on a femur bone, a tibia part 26 with a shaft 28 for anchoring on a tibia bone, and a meniscus part 30 arranged between the tibia part 26 and the femur part 24.

A bone contact surface 32 as well as a joint surface 34, which interacts with a corresponding joint surface 36 of the joint implant part 18 after implantation, are formed on the femur part 24.

In the xy-plane represented in FIG. 1, it is primarily a matter of outer surfaces of the joint implant part 14, i.e., in particular, of the bone contact surface 32 and the joint surface 34. Here attention is paid to an expedient distribution of the elasticity in the area of contact with a bone. As represented schematically in FIG. 5, a bone contact surface region 38 is defined and delimited in relation to an inner region 40 of the joint implant part 14. The bone contact surface region 38 defines a bone contact surface 42, which lies with surface-to-surface contact against a prepared bone surface 44 of a bone 46 represented partially in FIG. 5.

A structure of the bone contact surface region 38 is adapted to a structure of the prepared bone 46. As is clearly apparent from FIG. 5, a plurality of cavities 48 of different size are formed in the bone contact surface region 38 so that a porous structure is formed, which corresponds to a structure of the bone 46 which likewise has a plurality of cavities of different size. Owing to this configuration of the bone contact surface region 38, an elasticity of this region of the joint implant part 14 is so configured and predefined that the elasticity corresponds approximately to the elasticity of the prepared bone 46. Accordingly, as described, this can be achieved, on the one hand, in particular, by way of the inner structure of the bone contact surface region 38, and, on the other hand, by way of the material or materials used to produce the joint implant part 14.

The yz-plane 12 designated in FIG. 1 symbolizes, as described, a section through the implant. A schematic sectional view of, for example, the joint implant part 14 is represented in FIG. 4.

In FIG. 4, three different volume regions are also represented schematically and by way of example, namely a first volume region 52, which defines a bone contact surface region 54 with a bone contact surface 56, a second volume region 58, which defines a joint surface region 60 with a joint surface 62, and a third volume region 64. This has neither a bone contact surface nor a joint surface, i.e., it is located entirely in the interior of the joint implant part 14.

The volume regions 52, 58 and 64 indicated schematically in FIG. 4, therefore, respectively form a part of the joint implant part 14. It is possible for further volume regions of each kind of the three volume regions, having the stated characteristics, to be defined in a joint implant part.

A main aim of formation in the yz-plane is the lightweight construction of the joint implant part 14. On the basis of theoretical considerations, for example, by means of calculations using finite element methods, regions subjected to different levels of stress can be located on the joint implant part 14. To enable sufficient stability of the joint implant part 14 to be ensured, regions subjected to high stress are then constructed so as to be more stable than regions subjected to less or no stress.

Measures for the lightweight construction constitute, in particular, the omission of material in larger or smaller amounts. This is brought about by the formation of cavities 66 in those regions which are less highly stressed, i.e., require less firmness than highly stressed regions. This can be read, for example, directly in FIG. 4 from how great a density of the cavities 66 is. Cavities 66 can be formed, for example, in edge regions, i.e., up to the joint surface 34 or to the bone contact surface 32.

The bone contact surface 32 is, in particular, a surface for anchoring or fixing the joint implant part 14 to the bone. The anchoring and fixing can in this way be significantly influenced. An open-pored structure of the bone contact surface 32 enables bone to grow into the joint implant part.

A less firm structure of the joint implant part 14 can also be formed completely invisibly, for example, when a smooth, polished surface 68 is required, which interacts with the joint surface 34 of the further joint implant part 18. A reduction of the weight is of great interest, in particular, in extension shafts of knee revision endoprostheses. The omission of material and, therefore, a reduction in the weight of the joint implant part is also important in regions of a hip shaft of a hip joint endoprosthesis that are subjected to less stress.

The described joint implant parts can be formed, in particular, by sintering, for example, laser sintering, from a single material. Alternatively, one, two or more further materials may also be mixed with a basic material. This may be, for example, a metal powder containing cobalt, chromium and/or molybdenum, which is optionally mixed with a plastic material, for example, polyetheretherketone and is then sintered with a laser.

In the three different volume regions 52, 58 and 64, the proportions of the materials may be different. Furthermore, the cavities 66 may also be formed so as to be different in size and different in number. In this way, extents of elasticity with different moduli of elasticity can be almost optionally adjusted in dependence upon an implant thickness.

A total of three different, continuous extents of elasticity 70, 72 and 74, which can be achieved with the described method for formation of joint implant parts, are represented by way of example in FIG. 3. The extent of elasticity 70 shows schematically a linear dependency of the elasticity on an implant thickness. The extent of elasticity 72 shows a higher elasticity with a comparable implant thickness than the extent of elasticity 70. The extent of elasticity 74 shows schematically a lower elasticity in comparison with the extent of elasticity 70 with increasing implant thickness.

In comparison with the possible extents of elasticity 70, 72 and 74, an extent of elasticity 76, which is obtained with a uniform structural composition as is customary in implants available on the market, is represented in FIG. 3. Independently of an implant thickness, an elasticity of the joint implant part is, in this case, substantially constant.

With the above-described method in accordance with the invention, it is, in particular, possible to achieve component optimizations, which enable the formation of, for example, joint implant parts 14 with a reduced mass. These clearly improve the well-being of the patient. In addition, component optimizations are possible in all dimensions. It is, in particular, possible to both influence an elasticity in the interior of the joint implant part and to vary an elasticity in dependence upon an implant thickness. Furthermore, an elasticity of the joint implant part can also be adapted in the area of bone contact to the elasticity of a bone of a human being or an animal.

The described methods are, in principle, usable for all kinds of joint implant parts, i.e., in particular, for the formation of joint implant parts of hip and knee joint endoprostheses in all areas of care, i.e., for initial treatment and revision and also for tumor treatment of a patient.

The proposed laser sintering for formation of the joint implant parts makes it possible, in particular, to make use of all of the options which this method makes available. The creation of structures, formations and material compositions, which are inconceivable with hitherto existing, casting methods or machining methods with material removal, is made possible by the additive construction of joint implant parts.

With the proposed methods, it is possible to form implants in which both an optimization of a component geometry in dependence upon a weight and, in addition, a change in elasticity in dependence upon a material thickness can be taken into consideration.

Various kinds of joint implant parts, which enable a long-lasting stability and a significantly improved interaction with remaining bone of the patient, can be formed in the manner described above and made available to doctors for implantation.

LIST OF REFERENCE NUMERALS

10 xy-plane
12 yz-plane
14 joint implant part
16 joint endoprosthesis
18 joint implant part
20 joint implant part
22 knee joint endoprosthesis
24 femur part
26 tibia part
28 shaft
30 meniscus part
32 bone contact surface
34 joint surface
36 joint surface
38 bone contact surface region
40 inner region
42 bone contact surface
44 bone surface
46 bone
48 cavity
50 cavity
52 first volume region
54 bone contact surface region
56 bone contact surface
58 second volume region
60 joint surface region
62 joint surface
64 third volume region
66 cavity
68 surface
70 extent of elasticity
72 extent of elasticity
74 extent of elasticity
76 extent of elasticity

What is claimed is:

1. A joint implant part of a joint endoprosthesis, comprising:
at least one first volume region,
at least one second volume region, and
at least one third volume region,
the at least one first volume region defining a bone contact surface region with at least one bone contact surface, the at least one second volume region defining a joint surface region with at least one joint surface, and the at least one third volume region does not contact a bone surface or a joint surface in an implanted position,
wherein:
a modulus of elasticity of at least one of the at least one first, second, and third volume regions varies in at least one spatial direction,
the at least one first, second, and third volume region each comprises a plurality of cavities,
a total volume defined by the plurality of cavities in an entirety of the at least one third volume region is greater than a total volume defined by the plurality of cavities in an entirety of the at least one first volume region and greater than a total volume defined by the plurality of cavities in an entirety of the at least one second volume region;

compared total volumes of the at least one first volume region, the at least one second volume region and the at least one third volume region are identical in size, and an average total volume defined by the plurality of cavities in the at least one first volume region increases starting from the at least one bone contact surface in a direction towards the at least one third volume region, an average total volume defined by the plurality of cavities in the at least one third volume region has a maximum in the at least one third volume region, and an average total volume defined by the plurality of cavities in the at least one second volume region decreases in a direction towards the at least one joint surface.

2. The joint implant part in accordance with claim 1, wherein at least one of:
 a) a firmness at least one of in the at least one first, second, and third volume regions varies in at least one spatial direction,
and
 b) the at least one first volume region has an elasticity with a modulus of elasticity which corresponds to a modulus of elasticity of a bone of a human being or an animal,
and
 c) the at least one first volume region has an elasticity with a modulus of elasticity in a region of the at least one bone contact surface, which corresponds to a modulus of elasticity of a bone of a human being or an animal.

3. The joint implant part in accordance with claim 2, wherein the at least one first volume region, the at least one second volume region, and the at least one third volume region each respectively extend over approximately 1/3 of a thickness of the implant part, the thickness being defined by a distance between the at least one bone contact surface and the at least one joint surface.

4. The joint implant part in accordance with claim 1, wherein at least one of:
 a) a modulus of elasticity of at least one of the at least one first and the at least one second and the at least one third volume region lies in a range of from approximately 0.2 kN/mm$^2$ to approximately 100 kN/mm$^2$,
and
 b) the firmness of at least one of the at least one first and the at least one second and the at least one third volume region lies in a range of from approximately 0.2 kN/mm$^2$ to approximately 100 kN/mm$^2$,
and
 c) the at least one first volume region has an inner structure with physical characteristics which correspond to physical characteristics of an inner construction of a bone of a patient,
and
 d) the joint implant part is of one-piece formation.

5. The joint implant part in accordance with claim 4, wherein the at least one first volume region, the at least one second volume region, and the at least one third volume region each respectively extend over approximately 1/3 of a thickness of the implant part, the thickness being defined by a distance between the at least one bone contact surface and the at least one joint surface.

6. The joint implant part in accordance with claim 1, wherein the joint implant part is produced by sintering from at least one sinterable material.

7. The joint implant part in accordance with claim 6, wherein the at least one sinterable material is at least one of a metal and a plastic material.

8. The joint implant part in accordance with claim 7, wherein at least one of:
 a) the metal is or contains at least one of cobalt, chromium and molybdenum,
and
 b) the plastic material is or contains polyetheretherketone.

9. The joint implant part in accordance with claim 6, wherein the at least one first volume region, the at least one second volume region, and the at least one third volume region each respectively extend over approximately 1/3 of a thickness of the implant part, the thickness being defined by a distance between the at least one bone contact surface and the at least one joint surface.

10. The joint implant part in accordance with claim 1, wherein:
 at least one of the at least one first, the at least one second, and the at least one third volume region is/are formed from different materials,
 wherein a proportion of different materials in a transition between two of the three different volume regions varies in at least one spatial direction.

11. The joint implant part in accordance with claim 10, wherein the at least one first volume region, the at least one second volume region, and the at least one third volume region each respectively extend over approximately 1/3 of a thickness of the implant part, the thickness being defined by a distance between the at least one bone contact surface and the at least one joint surface.

12. The joint implant part in accordance with claim 1, wherein at least one of:
 a) the plurality of cavities are in the form of a closed, completely enclosed cavity,
and
 b) at least some of the plurality of cavities are in fluid communication with one another,
and
 c) at least one of the plurality of cavities is in the form of a depression of the bone contact surface,
and
 d) the at least one joint surface at least one of is in the form of a closed layer of material and is smooth and is polished.

13. The joint implant part in accordance with claim 12, wherein the at least one first volume region, the at least one second volume region, and the at least one third volume region each respectively extend over approximately 1/3 of a thickness of the implant part, the thickness being defined by a distance between the at least one bone contact surface and the at least one joint surface.

14. The joint implant part in accordance with claim 1, wherein the joint implant part is produced by sintering at least two materials that are mixed before the sintering.

15. The joint implant part in accordance with claim 1, wherein the at least one first volume region, the at least one second volume region, and the at least one third volume region each respectively extend over approximately 1/3 of a thickness of the implant part, the thickness being defined by a distance between the at least one bone contact surface and the at least one joint surface.

16. A joint endoprosthesis comprising at least one joint implant part, the at least one joint implant part comprising:

at least one first volume region,
at least one second volume region, and
at least one third volume region,
the at least one first volume region defining a bone contact surface region with at least one bone contact surface, the at least one second volume region defining a joint surface region with at least one joint surface, and the at least one third volume region does not contact a bone surface or a joint surface in an implanted position,
wherein:
a modulus of elasticity of at least one of the at least one first, second, and third volume regions varies in at least one spatial direction,
the at least one first, second and third volume regions each comprises a plurality of cavities,
a total volume defined by the plurality of cavities in an entirety of the at least one third volume region is greater than a total volume defined by the plurality of cavities in an entirety of the at least one first volume region and greater than a total volume defined by the plurality of cavities in an entirety of the at least one second volume region,
compared total volumes of the at least one first volume region, the at least one second volume region and the at least one third volume region are identical in size, and
an average total volume defined by the plurality of cavities in the at least one first volume region increases starting from the at least one bone contact surface in a direction towards the at least one third volume region, an average total volume defined by the plurality of cavities in the at least one third volume region has a maximum in the at least one third volume region, and an average total volume defined by the plurality of cavities in the at least one second volume region decreases in a direction towards the at least one joint surface.

17. The joint endoprosthesis in accordance with claim 16, wherein the joint endoprosthesis is in the form of one of a knee joint, hip joint, ankle joint, elbow joint or shoulder joint endoprosthesis.

18. The joint endoprosthesis in accordance with claim 16, wherein the at least one first volume region, the at least one second volume region, and the at least one third volume region each respectively extend over approximately 1/3 of a thickness of the implant part, the thickness being defined by a distance between the at least one bone contact surface and the at least one joint surface.

19. A joint implant part of a joint endoprosthesis, comprising:
at least one first volume region,
at least one second volume region, and
at least one third volume region,
the at least one first volume region defining a bone contact surface region with at least one bone contact surface, the at least one second volume region defining a joint surface region with at least one joint surface, and the at least one third volume region does not contact a bone surface or a joint surface in an implanted position,
wherein:
a modulus of elasticity of at least one of the at least one first, second, and third volume regions varies in at least one spatial direction,
the at least one first, second, and third volume region each comprises a plurality of cavities,
a total volume defined by the plurality of cavities in an entirety of the at least one third volume region is greater than a total volume defined by the plurality of cavities in an entirety of the at least one first volume region and greater than a total volume defined by the plurality of cavities in an entirety of the at least one second volume region;
compared total volumes of the at least one first volume region, the at least one second volume region and the at least one third volume region are identical in size, and
the at least one first volume region, the at least one second volume region, and the at least one third volume region each respectively extend over approximately 1/3 of a thickness of the implant part, the thickness being defined by a distance between the at least one bone contact surface and the at least one joint surface.

* * * * *